United States Patent
Crowell (10) Patent No.: US 10,864,338 B2
(45) Date of Patent: Dec. 15, 2020

(54) RESCUE BREATHING APPARATUS

(71) Applicant: Mark A. Crowell, Mountain Top, PA (US)

(72) Inventor: Mark A. Crowell, Mountain Top, PA (US)

(73) Assignee: Austere Medical Group, LLC, Mountain Top, PA (US)

(*) Notice: Subject to any disclaimer, the term of this patent is extended or adjusted under 35 U.S.C. 154(b) by 193 days.

(21) Appl. No.: 15/983,963

(22) Filed: May 18, 2018

(65) Prior Publication Data

US 2018/0361092 A1    Dec. 20, 2018

Related U.S. Application Data

(60) Provisional application No. 62/508,765, filed on May 19, 2017.

(51) Int. Cl.
| | | |
|---|---|---|
| *A61M 16/04* | (2006.01) |
| *A62B 7/00* | (2006.01) |
| *A61M 16/08* | (2006.01) |
| *A61M 16/20* | (2006.01) |
| *A61M 16/00* | (2006.01) |

(52) U.S. Cl.
CPC .... *A61M 16/0463* (2013.01); *A61M 16/0048* (2013.01); *A61M 16/208* (2013.01); *A62B 7/00* (2013.01); *A61M 16/0078* (2013.01); *A61M 16/0875* (2013.01)

(58) Field of Classification Search
CPC .......... A61M 16/0048; A61M 16/0078; A61M 16/0463; A61M 16/0875; A61M 16/208; A61M 16/0084; A62B 7/00
See application file for complete search history.

(56) References Cited

U.S. PATENT DOCUMENTS

| | | | | |
|---|---|---|---|---|
| 3,017,880 A * | 1/1962 | Brook | ............... | A61M 16/0048 128/203.11 |
| 3,089,485 A * | 5/1963 | Hirschhorn | ....... | A61M 16/0495 128/202.28 |
| 3,262,445 A * | 7/1966 | Stults | ..................... | A47J 36/30 126/262 |
| 3,548,822 A * | 12/1970 | Seeler | ............... | A61M 16/0048 128/203.11 |
| 4,446,864 A * | 5/1984 | Watson | ............. | A61M 16/0463 128/202.28 |
| 4,521,038 A * | 6/1985 | Cerny | ................... | A61M 16/08 128/202.27 |
| 4,535,765 A * | 8/1985 | Paoluccio | ......... | A61M 16/0048 128/203.11 |
| 4,676,239 A * | 6/1987 | Humphrey | ............ | A61M 16/08 128/203.28 |
| 5,062,420 A * | 11/1991 | Levine | .................. | A61M 16/08 128/204.18 |
| 5,152,283 A * | 10/1992 | Yamasaki | ......... | A61M 16/0048 128/202.28 |
| 5,355,876 A * | 10/1994 | Brodsky | ........... | A61M 16/0463 128/202.27 |

(Continued)

*Primary Examiner* — Samchuan C Yao
*Assistant Examiner* — Nathan M Le
(74) *Attorney, Agent, or Firm* — Vos-IP, LLC (57) ABSTRACT

A rescue tube comprising a tube having a first and second end, a one-way valve and a ported double swivel elbow; wherein the one-way valve and ported double swivel elbow are connected to one another, and the one-way valve is attached to the tube.

15 Claims, 6 Drawing Sheets

(56) References Cited

U.S. PATENT DOCUMENTS

| | | | | |
|---|---|---|---|---|
| 5,485,835 A * | 1/1996 | Vande Streek | A61M 15/02 | 128/203.12 |
| 5,557,049 A * | 9/1996 | Ratner | A61M 16/208 | 128/204.23 |
| 5,558,371 A * | 9/1996 | Lordo | A61M 16/0057 | 128/205.13 |
| 5,694,922 A * | 12/1997 | Palmer | A61M 16/0463 | 128/202.27 |
| 5,762,063 A * | 6/1998 | Coates | A61M 16/0463 | 128/202.27 |
| 5,823,184 A * | 10/1998 | Gross | A61M 16/08 | 128/204.18 |
| 6,029,539 A * | 2/2000 | Young | F16F 15/131 | 74/574.3 |
| 6,123,075 A * | 9/2000 | Kirk | A61M 16/0078 | 128/203.11 |
| 6,612,304 B1 * | 9/2003 | Cise | A61M 16/0463 | 128/200.26 |
| 6,615,835 B1 * | 9/2003 | Cise | A61M 16/0463 | 128/207.14 |
| 6,631,713 B1 * | 10/2003 | Christopher | A61M 16/0488 | 128/200.21 |
| 7,147,252 B2 * | 12/2006 | Teuscher | A61M 16/08 | 285/280 |
| 7,556,041 B2 * | 7/2009 | Madsen | A61M 16/0463 | 128/207.14 |
| 8,181,649 B2 * | 5/2012 | Brunner | A61M 16/08 | 128/204.23 |
| 8,459,256 B2 * | 6/2013 | Roblejo | A61M 16/0048 | 128/203.11 |
| 8,550,076 B2 * | 10/2013 | Nashed | A61M 16/0009 | 128/203.28 |
| 8,826,905 B2 * | 9/2014 | Nashed | A61M 16/085 | 128/203.28 |
| 10,413,687 B2 * | 9/2019 | Millar | A61M 16/0833 | |
| 2001/0012923 A1 * | 8/2001 | Christopher | A61M 16/085 | 604/48 |
| 2002/0117173 A1 * | 8/2002 | Lynn | A61M 16/0078 | 128/202.28 |
| 2004/0099273 A1 * | 5/2004 | Wright | A61M 16/0084 | 128/207.18 |
| 2005/0139220 A1 * | 6/2005 | Christopher | A61M 16/0495 | 128/207.14 |
| 2007/0049841 A1 * | 3/2007 | Lepel | A61M 16/0833 | 600/534 |
| 2008/0041391 A1 * | 2/2008 | Worley | A61M 16/0465 | 128/207.14 |
| 2008/0251082 A1 * | 10/2008 | Sinha | A61M 16/1065 | 128/207.16 |
| 2009/0071482 A1 * | 3/2009 | Huddlestone | A61M 16/0084 | 128/205.13 |
| 2016/0038700 A1 * | 2/2016 | White | A61M 16/208 | 128/202.27 |
| 2017/0095631 A1 * | 4/2017 | Fukunaga | A61M 16/125 | |

\* cited by examiner

RESCUE BREATHING APPARATUS

PRIORITY CLAIM

This application claims priority to U.S. Provisional Patent Application No. 62/508,765, filed May 19, 2017.

FIELD OF INVENTION

The present application is related to a breathing apparatus, for providing rescue breathing to a patient who is either limited in their ability to breathe, or is unable to breathe.

BACKGROUND OF INVENTION

Current rescue breathing technology is primarily related to direct mouth-to-mouth CPR and breathing bags. Breathing bags, such as those by AMBU® are compressible bags that compress the air in the bag and allow that air to be directed towards the lungs of a patient in need of breathing support. The breathing bags are single use devices and have been in use for decades.

To use an AMBU® bag, the bag is connected to an endotracheal tube, which is inserted into the patient's mouth and into the esophagus. Once the endotracheal tube is inserted, the bag is compressed to provide air. While these devices have had a long history of success, they suffer from several issues, specifically related to their single direction of functionality, size, and cost. For example, one issue is that the bag needs to be attached to the endotracheal tube with a particular orientation. Accordingly, once the bag is attached to the tube, the components must be held in that orientation to prevent the tube from being displaced from the patient. Furthermore, the bag is placed nearly on the patient's face, and movement of the patient or other obstacles near the patient's mouth can be problematic for both sufficient compression or even just for use of the device at all. Accordingly, as the bag needs to have sufficient space to be compressed, in certain instances, it is nearly impossible to properly use such a bag or to keep the endotracheal tube properly inserted into the patient for rescue breathing.

Bags can also be attached directly to a face mask, instead of a tube. Again, this poses the same issue with regard to proximity and obstacles in front of the patient's face, to prevent appropriate rescue breathing.

SUMMARY OF INVENTION

The following presents a simplified summary of the invention in order to provide a basic understanding of some aspects of the invention. This summary is not an extensive overview of the invention. It is not intended to identify key/critical elements of the invention or to delineate the scope of the invention. Its sole purpose is to present some concepts of the invention in a simplified form as a prelude to the more detailed description that is presented later.

In a particular embodiment, a rescue breathing apparatus comprises a flexible tubing having a patient side end and a rescue side end (opposing ends of the tube), the patient side end connected to an adapter, which connects to a one-way valve. The one-way valve has a first and second end, the first connected to the adapter the opposing end connected to a double swivel elbow. The rescue side end of the tube is connected to a mouthpiece to allow for air to be generated through the tube.

In a particular embodiment, the double swivel elbow is connected to an airway generating device, including but not limited to an endotracheal intubation, surgical crichothyroidotomy, an airway adjunct, or a facemask. The rescue side end of the rescue breathing apparatus is connected to a mouthpiece, wherein a breath can be provided by rescue personnel. Alternatively, an air compression bag can replace the mouthpiece and be compressed by hand or mechanical force to provide air. Alternatively, an air compression machine can provide air through the tube.

A particular embodiment is directed towards a rescue tube comprising a tube having a first and second end, a one-way valve and a ported double swivel elbow; wherein the one-way valve and ported double swivel elbow are connected to one another, and the one-way valve is attached to the tube. The rescue tube further comprising a first adapter disposed of between the first end of said tube and the one-way valve. The rescue tube further comprising a second adapter disposed of on the second end of said tube. The rescue tube wherein said ported double swivel elbow is a "y" shaped apparatus comprising a first and second opening, and a port. In certain embodiments, said ported double swivel has said first opening attached to a one-way valve and said second open attached to an airway adjunct. In certain embodiments, the double swivel elbow comprises an accordion portion.

A method of providing rescue breathing to a patient comprising intubating said patient with an airway adjunct; attaching to said airway adjunct a rescue tube comprising a tube having a first and second end, a one-way valve and a ported double swivel elbow; wherein the one-way valve and ported double swivel elbow are connected to one another, and the one-way valve is attached to the tube; breathing into said second end of said tube. The method wherein said second end of said tube comprises a mouth piece. The method wherein further comprising attaching to said second end of said tube a bag device capable of being compressed to provide air to said patient, and compressing said bag to perform the step of breathing into said second end of said tube.

A preferred embodiment is directed towards a rescue tube comprising a tube having a proximal and distal end, and attached to the proximal end is a one-way valve, said one-way valve having a flow end and a check end, and allowing flow of air from the distal end to the proximal end, and attached to the check end of the one-way valve is a ported double swivel elbow having a long arm and a short arm, and wherein the long arm and short arms are attached at an angle with a passage allowing passage of gas through the short and long ends to the opening at each end, wherein the opening on the short arm is attached to the check end of the one-way valve, wherein the opening on the long arm is suitable for connection to a breathing device; and wherein connected to the distal end of said tube is a mouthpiece.

In preferred embodiments, the rescue tube further comprising a first adapter disposed of between the proximal end of said tube and the flow end of the one-way valve.

In preferred embodiments, the rescue tube further comprising a second adapter disposed of on the distal end between the distal end of the tube and the mouthpiece.

In preferred embodiments, the rescue tube wherein said ported double swivel elbow is a "y" shaped apparatus made of the short and long arms, and a port in the short arm, and comprising an accordion structure on the long arm, said accordion structure capable of extending in length and flexing at least 90 degrees.

In preferred embodiments, the rescue tube wherein said breathing device is an airway adjunct. In preferred embodiments, the rescue tube wherein said airway adjunct is an endotracheal tube.

In a preferred embodiment, a method of providing rescue breathing to a patient comprising intubating said patient with an airway adjunct; attaching to said airway adjunct a rescue tube comprising a tube having a proximal and distal end, and attached to the proximal end is a one-way valve, said one-way valve having a flow end and a check end, and allowing flow of air from the distal end to the proximal end, and attached to the check end of the one-way valve is a ported double swivel elbow having a long arm and a short arm, and wherein the long arm and short arms are attached at an angle with a passage allowing passage of gas through the short and long ends to the opening at each end, wherein the opening on the short arm is attached to the check end of the one-way valve, wherein the opening on the long arm is connected to the airway adjunct; and wherein connected to the distal end of said tube is an air imparting component capable of forcing air through the tube and into the airway adjunct; forcing air through the tube and into the airway adjunct to generating a breath to the patient; allowing the patient to exhale the forced air.

The method wherein the air imparting component is a mouthpiece.

The method wherein a second person breathes into the mouthpiece to force air through the tube.

The method wherein the air imparting component is a breathing bag.

The method wherein the breathing bag is compressed to force air through the tube.

A further preferred embodiment defining a rescue tube comprising a length of flexible tubing, defining a passage between a proximal and distal end of said tube, and attached to the proximal end of said tube is a one-way valve, said one-way valve having a flow end and a check end, with said one-way valve oriented with the proximal end of said tube engaged to the flow end of said one-way valve thereby allowing flow of air from the distal end to the proximal end of said tube, and attached to the check end of the one-way valve is a ported double swivel elbow having a long arm and a short arm, and wherein the long arm and short arms are attached at an angle with a passage allowing passage of gas through the short and long ends to the opening at each end, wherein the opening on the short arm is attached to the check end of the one-way valve, wherein the opening on the long arm is suitable for connection to a breathing device; and wherein connected to the distal end of said tube is air imparting structure.

In preferred embodiments, the rescue tube wherein said short arm comprises a self-sealing port.

In preferred embodiments, the rescue tube wherein the ported double swivel elbow comprises an accordion structure on the long arm, said accordion structure capable of bending. In preferred embodiments, the rescue tube wherein said accordion structure is capable of bending at least 90 degrees. In preferred embodiments, the rescue tube wherein said accordion structure is capable of extending in length.

In preferred embodiments, the rescue tube said tube having an inner diameter between 10 and 25 mm.

In preferred embodiments, the rescue tube further comprising an adaptor defined to connect between the proximal end of said tube and said one-way valve.

In preferred embodiments, the rescue tube further comprising an adaptor defined to connect to the distal end of said tube, and wherein an air imparting structure is connected to said adaptor. In preferred embodiments, the rescue tube wherein said air imparting structure is selected from: a mouthpiece; said mouthpiece comprising an insertion end connected to said adaptor, and a breath giving end; said breath giving end comprising a flange, a breathing bag, or a mechanical air flow generating machine.

DETAILED DESCRIPTION OF THE EMBODIMENTS

In a medical situation whether in military operation or emergency events, there are situations where rescue breathing must be provided to an unconscious patient whom requires an airway to maintain oxygen to the lungs. In most instances today, a breathing bag, such as those by AMBU®, is frequently utilized, which can be held on the patient and compressed to force air into the lungs. The bag is directly attached to an endotracheal tube, and once the tube is inserted, the bag is compressed. After the patient's lungs are filled with air through the compression of the bag, the lungs, due to the weight of the cavity, decompress the forced air, and exhale the air, thus completing a single "breath." After compression, the bag re-inflates and the process can be repeated. Subsequently, another compression may proceed, to again force a breath into the patient.

However, performing this procedure requires that at least one hand from rescue personnel is placed onto the bag to perform these compressions. In some instances, two hands would be required to properly compress the bag and to give sufficient breath to a patient. The loss of a hand, or hands is problematic in both military instances as well as in non-military emergency situations.

Indeed, as described herein is a rescue tube comprising components and features that allow for a user to maintain the use of their hands for other tasks, while providing rescue breathing to a patient. For example, breathing may be maintained, while the rescuer treats other wounds. In military situations, the rescuer may need hands to maintain a weapon or to remove both the rescuer and the injured from the battle field as urgently as possible, and thus having free hands to maneuver or manipulate additional devices is necessary. For example the rescuer can use both hands to lift and carry the injured away from the battlefield.

The rescue tube functions as an extension between the provider and the patient. However, the patient must first have a breathing tube inserted. Examples of breathing tubes include endotracheal tubes, as well as mouth insertion devices, for example, comprising cuffs to enter the trachea. Examples including the King Airway® and Combitube®, though other brands and examples exist. In general, these devices are airway adjuncts, devices that can be placed into reach the trachea to provide oxygen. For mouth placed devices, these often include a balloon or cuff that blocks the esophagus to allow air to enter the trachea, to fill the lung.

Figure 1:
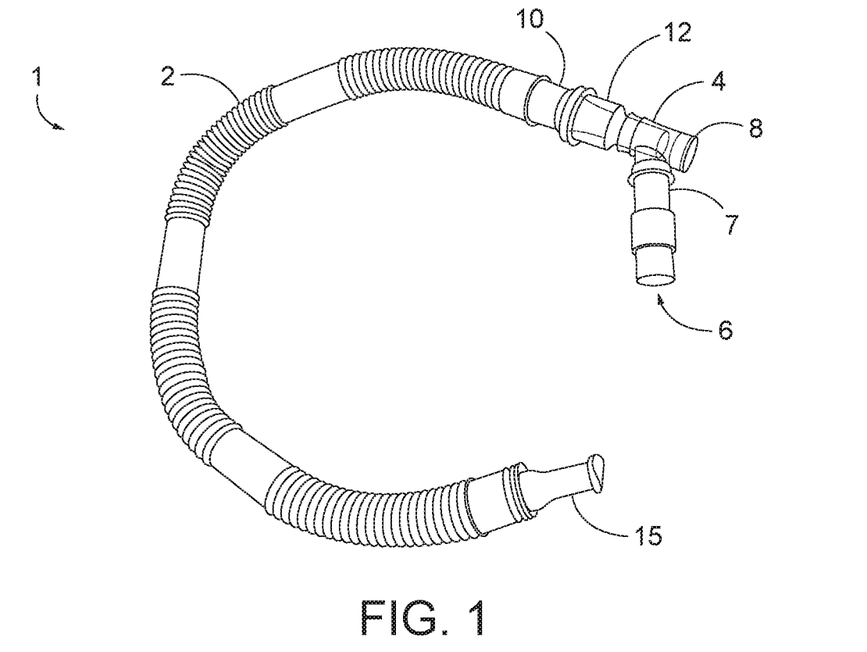
FIG. 1 depicts a rescue breathing apparatus.

The embodiments of the invention described herein, provide a novel device, a rescue tube, to connect to one or more breathing devices. For example, as depicted in FIG. 1, a rescue tube 1 is depicted. The rescue tube 1 comprises a length of tubing 2, said tubing have a proximal opening to the patient (patient end) 22 and a distal opening (rescue end) 21 and each of the proximal 22 and distal 21 ends providing passage of gas through the tube. In certain embodiments, the tube is a corrugated flexible polyurethane tubing having an outer diameter of about 5 to about 50 mm, with an inner diameter of about 4 to about 45 mm. Preferably the tube has an outer diameter of about 10-30 mm, with an inner diameter of about 9-28 mm. Most preferably, the tube is between about 10 and 22 mm, and each of the proximal 22 and distal ends 21 capable of receiving a second component. In certain embodiments, the tubing can be any flexible tubing that allows for the passage of gasses between the two ends.

Figure 7:
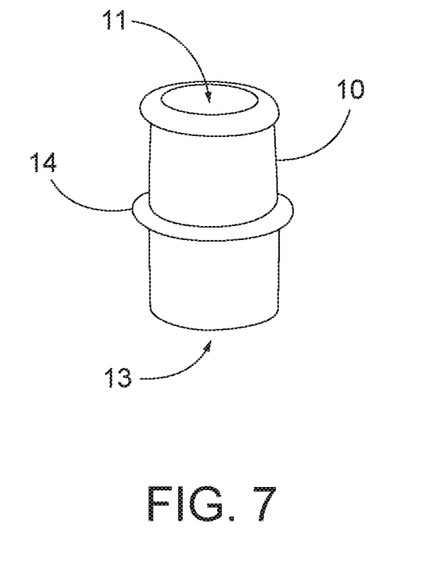
FIG. 7 depicts a component of a rescue breathing apparatus

Preferably, the second component to be received into the proximal 22 end of the tube 2 is an adaptor 10. For example, in the proximal 22 end of FIG. 1, an adaptor 10 is provided engaged into the proximal end 22, thus providing a new component for attaching additional parts. The adaptor 10 is depicted in FIG. 7 in detail, having a first adaptor end 11 and a second adaptor end 13, and a central connector junction 14 having a raised edge. The adaptor 10 is defined to have an outer diameter on the first end 11 and second end 13 to fit into the proximal end 22 of the tube. Accordingly, the adaptor is mated to have a corresponding outer diameter that mates with the inner diameter of the proximal end 22 of the tube. The proximal end 22 of the tube then mates onto the first end 11 as far as the central connector junction 14. The first end 11 and second end 13 of the adaptor are connected via a passage between each of the first end 11 and second end 13, thus the adaptor functions as an extension of the tube 2, allowing for passage of gasses through the adaptor 10.

The first end 11 and second end 13 of the adaptor are defined to be received into the proximal end 22 of the tube, on one end, and then to have a suitable outer or inner diameter to mate with the flow side opening 16 of the one-way valve 12. Accordingly, the adaptor 10 functions as one of ordinary skill in the art would expect it to function, it allows for connection of the proximal end of the tube 22 to the flow side opening 16 of the one-way valve. Those of skill in the art will recognize that the adaptor 10 is necessary only so far as the proximal end of the tube 22 requires such adaptor 10 to mate with the flow side opening 16 of the one-way valve. An appropriate tube diameter and corresponding diameter (or attachment means, for example those used by Leur Lock® or other known attachment means), would allow for exclusion of the adaptor 10.

Figure 8:
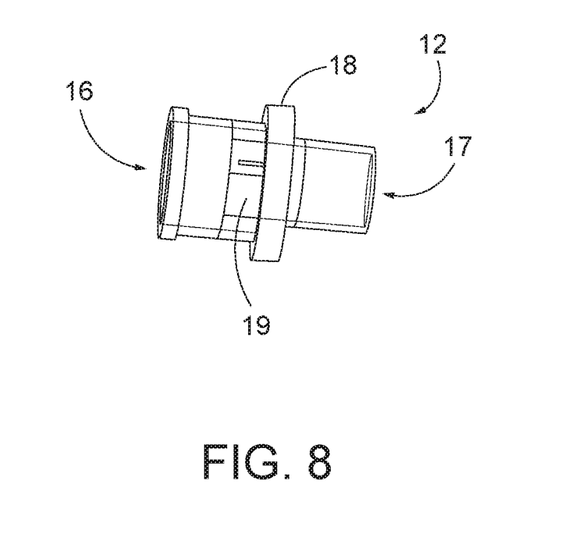
FIG. 8 depicts a component of a rescue breathing apparatus.

The one-way valve 12 functions to allow air to only flow through from the flow side opening 16 through the one-way valve internal valve 19 and through to the one-way valve check side. As those of ordinary skill in the art recognize, the one-way valve allows air flow only from the flow side 16 through to the check side 17. If air is pressed back from the check side 17, it will not pass through the internal valve 19, but will instead be released through the internal valve 19 (as a relief valve) to allow the air to exit the valve, but not proceed into the tube 2. Accordingly, this valve thus prevents passage of gasses back through this valve, and instead allows release of the exhaled gas.

Figure 2:
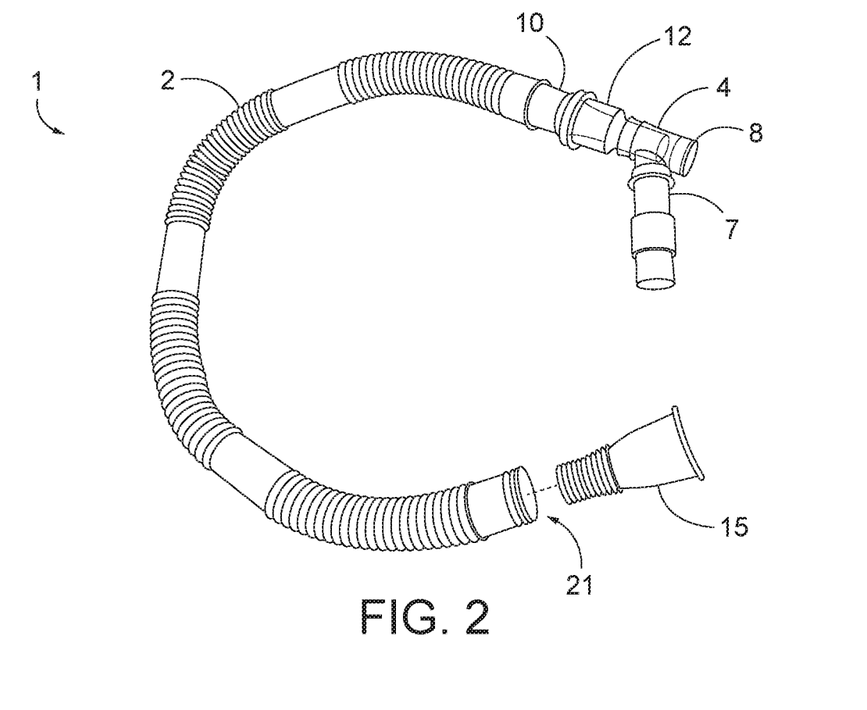
FIG. 2 depicts a partial exploded view of a rescue breathing device.
Figure 12:
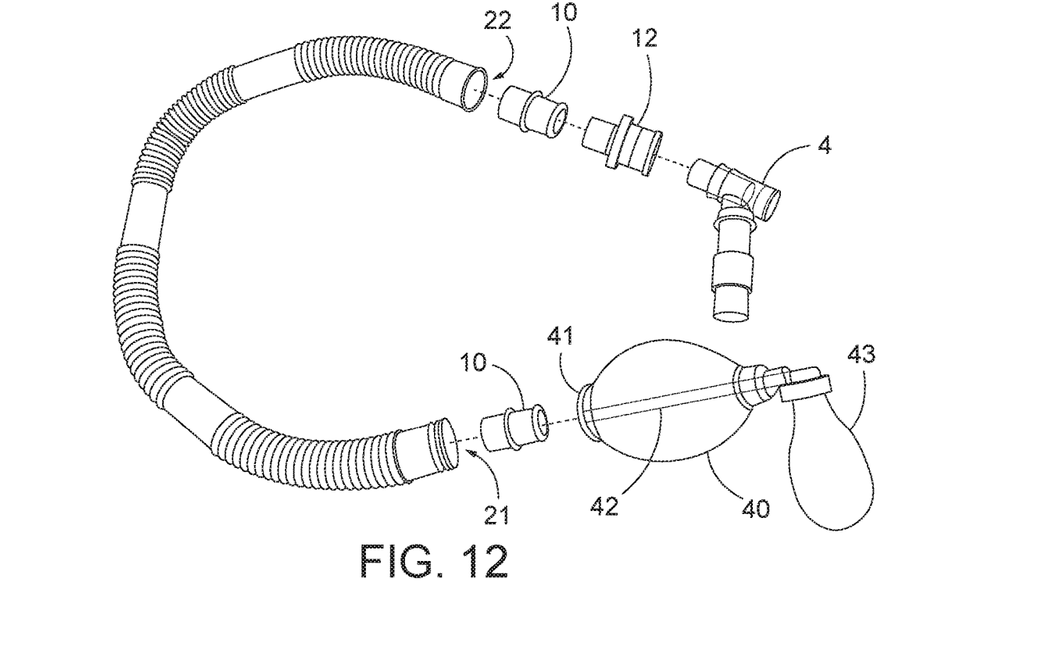
FIG. 12 depicts a rescue breathing apparatus with a breathing bag attached at the rescue side end of the tube.

The check side 17 then mates with a double swivel elbow 4. Finally, on the opposing end of the tube 2, (distal end of the tube 21) a mouthpiece 15 is attached. FIG. 2 specifically shows the mouthpiece 15 in the partial exploded view. The mouthpiece 15 will be inserted into the distal end of the tube 21. As with the proximal end of the tube 21, an adaptor 10 may be utilized, should one be necessary to mate the tube diameter to the diameter of one end of the mouthpiece 15. For example, the adaptor 10 is depicted in FIG. 12 attaching to the distal end 21, and attaching to a bag 40. As with the proximal end 22, the adaptor 10 is utilized to connect a further component to the flexible tubing.

Figure 3:
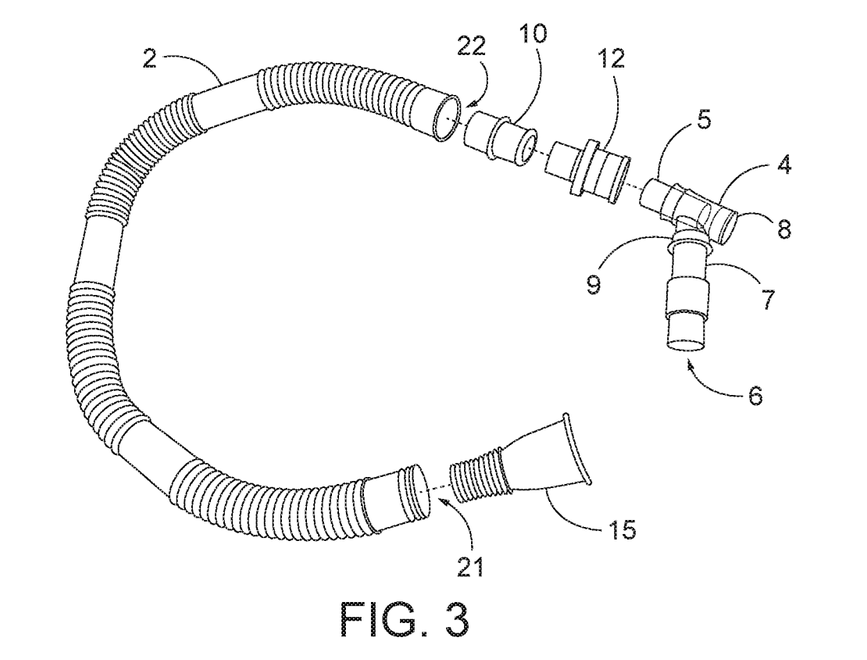
FIG. 3 depicts an exploded view of a rescue breathing device.

FIG. 3 provides an exploded view of each of the components in serial. The mouthpiece 15 connects into the distal end of the tube 21. Then the flexible length of tube 2 allows for passage of gasses from the distal end 21 through to the proximal end 22, before the proximal end 22 is inserted an adaptor 10. The adaptor 10 first end 11 mates with the proximal end 22 to an air tight seal (up to a sufficient PSI, to allow for rescue breathing). However, some air passage may occur in one or more of the connections without destroying the function of the device, should each connecting not be perfectly air tight for the force of air being provided.

Into the second end 13 of the adaptor 10 is the one-way valve 12. Into the check side 17 of the one-way valve is inserted the short arm 50 end 5 of the double swivel elbow 4. Air passes through the check valve from the flow side 16 through to the check side 17 and now into the double swivel elbow 4. The long arm 51 of the double swivel elbow 4 possesses a junction 9 to allow for complete rotation of the double swivel elbow 4. Further the elbow 4 contains a self-sealing port 8. The long arm 51 of the double swivel elbow 4 further optionally possesses an accordion structure 7 to allow for further rotation and movement of the elbow 4, and ending on the long arm with a long arm opening 6.

Figure 4:
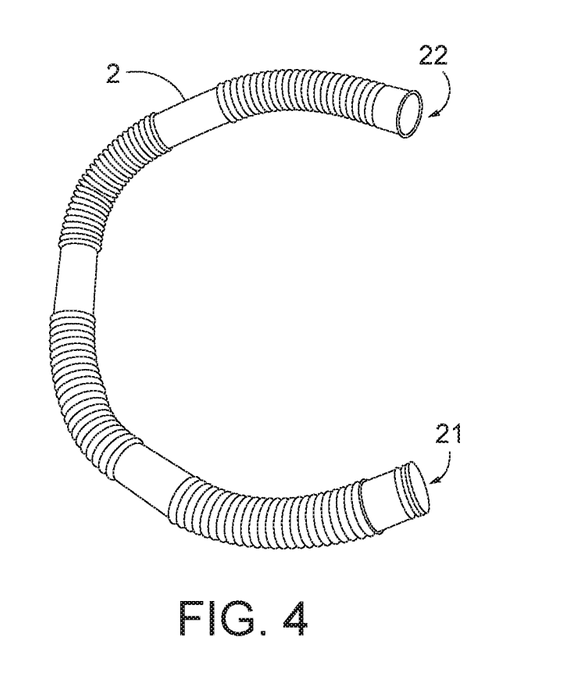
FIG. 4 depicts a component of a rescue breathing device.

FIG. 4 provides an embodiment of a tube 2. The tube can be any length of tubing allowing for passage of gas from the distal end 21 to the proximal end 22, and have openings at each end to either directly receive a second component, or to receive an adaptor. Typically, the openings allow an insertion into the inner diameter, or alternatively over the outer diameter of each of the proximal end 22 and distal end 21.

Figure 5:
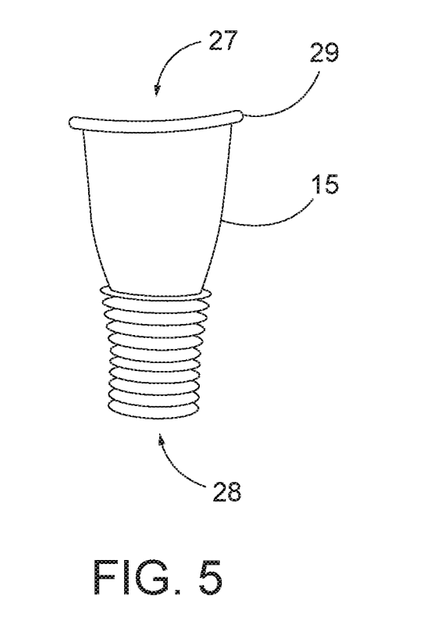
FIG. 5 depicts a component of a rescue breathing device.

FIG. 5 depicts the mouthpiece 15. Mouthpiece 15 comprises an insertion end 28 and a breath giving end 27. The breath giving end 27 is typically wider than the insertion end 28, and provides a comfortable fit for placing into the mouth of a rescuer. The breath giving end 27 comprises a raised flange 29. This raised flange 29 allows for the mouthpiece breath giving end 27 to be in the mouth, and the teeth or lips to hold the mouthpiece 15 without it slipping or falling out of the mouth. The breath giving end 27 is connected to the insertion end 28 with a passage, allowing for air to flow through the mouthpiece 15, and again act as an extension of a tubular structure.

Figure 6:
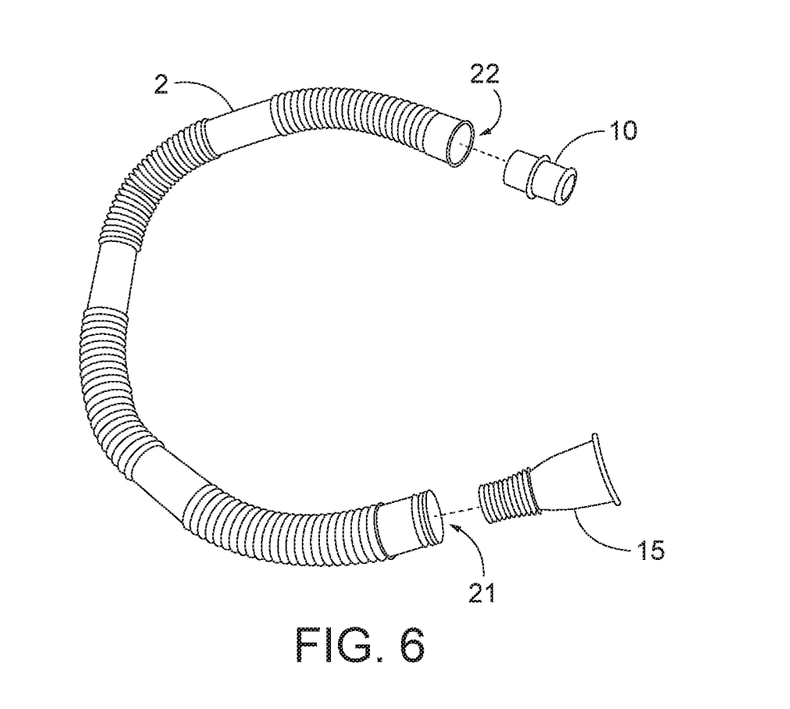
FIG. 6 depicts a partial exploded view of components of a rescue breathing apparatus.

FIG. 6 provides as simple exploded view of the mouthpiece 15 insertion end 28 as it would be inserted into the distal end 21 of the tube. Conversely, on the opposing side at the proximal end 22, the adaptor 10 would be inserted into the proximal end 22.

FIG. 7, as described above, briefly, provides for an embodiment of an adaptor 10. The precise dimensions of the adaptor may be modified based on the precise inner and outer dimensions of the components to be attached. Those of skill in the art recognize that each end of the adaptor can be the same or different sizes, and can attach both internally, or externally to a component on each end. The adaptor 10 should be of sufficient size to allow for secure fit into each component. In some embodiments, the rescue breathing device is assembled from a kit of components, and thus a mechanical, friction fit is appropriate. It may be suitable to have a portion of the adaptor 10, to possess an o-ring or other component on each end, to function as a gasket, to aid in the air-tight fit of the components.

However, the device may also be appropriately manufactured with components pre-attached, and this may include an adhesive suitable to attach such components. Where the rescue breathing device 1 is pre-manufactured, such features, like the adaptor 10 may be excluded, as the precise fit of the one-way valve 12 may be manufactured to fit into a proximal end 22 of the tube.

FIG. 8 details a one-way valve 12, having the flow side 16, the check side 17, a junction 18, and an internal valve 19. Those of skill in the art recognize that numerous designs exist for check valves. The valve must allow passage of air from the flow side 16 through the check side 17, but prevent flow of air from the check side 17 back to the flow side 16. This is so that when a patient is intubated, air can be blown or provided from the distal end 21 and flow through the one-way check valve 12, through the double swivel elbow 12 and through the endotracheal tube 23 and into the patient's lungs, but when the patient exhales, gas will not pass through the one-way valve 12. Furthermore, blood, saliva, vomit, and other bodily fluids from the mouth and stomach will not be passed through the one-way valve 12 to the rescuing person. The one-way valve allows flow in one direction from the rescuer flow side 16 to the patient (check side 17), however during the exhalation phase the exhaled air travels to the one-way valve 12 to the internal components 19 preventing return flow to the rescuer end however there is a relief valve where the exhaled air is removed from the system allowing. The patient to expire used air. This way there is room for new air to enter the Lungs.

Figure 9A:
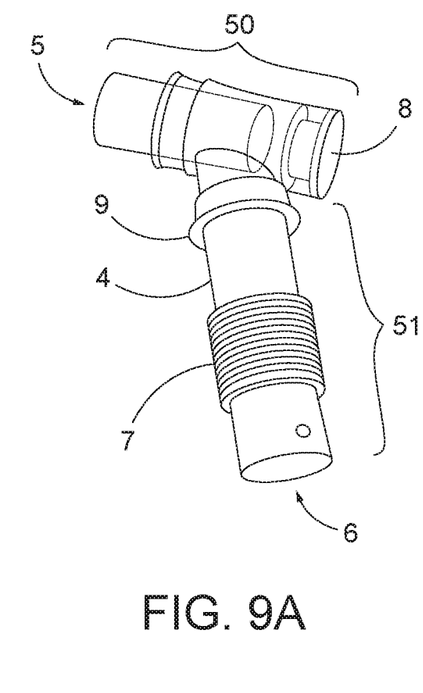
FIGS. 9A, 9B, and 9C depict various views of a component of a rescue breathing apparatus.
Figure 9B:
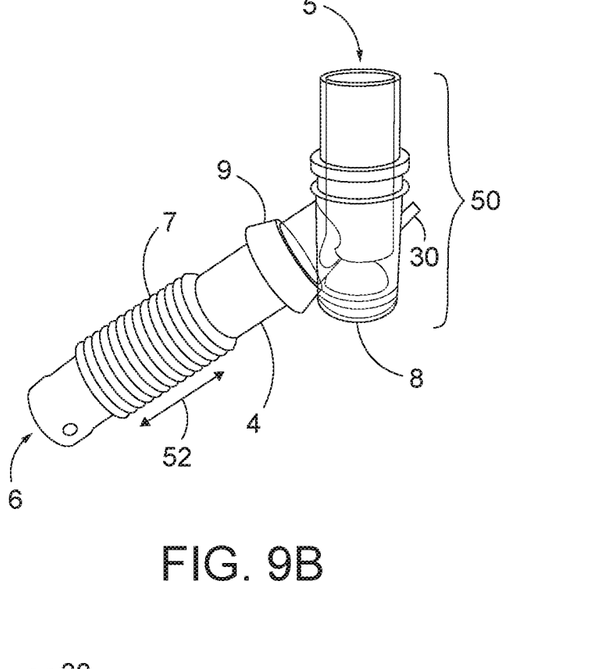
Figure 9C:
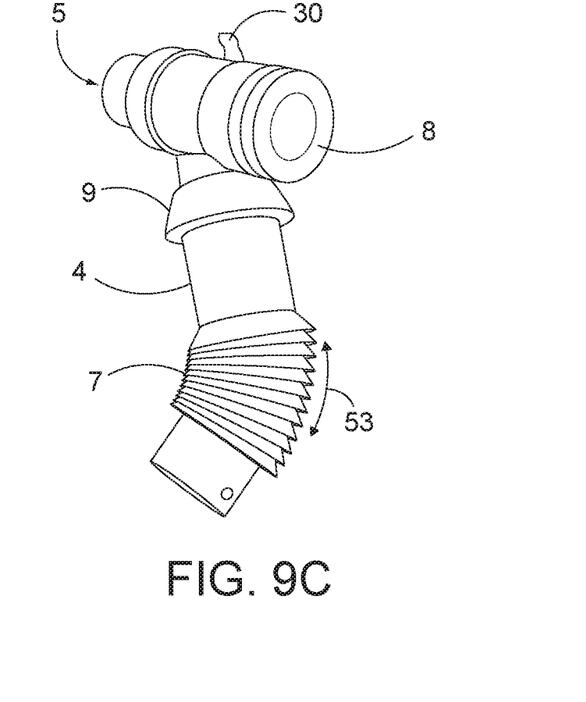

FIGS. 9A, 9B, and 9C detail portions of the double swivel elbow 4. The double swivel elbow 4 contains a short arm 50 and a long arm 51. On the short arm 50 is the short arm end 5 of the double swivel elbow 4. This short arm end 5 contains an outer/inner diameter sufficient to mate with the check side 17 of the one-way check valve 12. At the opposing end of the short arm 50 is a self-sealing port 8. This port can be utilized for further attachment of additional components. Indeed, the port may further accept an adapter to allow for attachment of such accessories. For example, oxygen may be attached at this point, or direct placement of other gasses for surgical procedures as non-limiting examples. Due to the nature of the self-sealing port, a needle or other tube can be inserted and withdrawn, if such insertion is necessary to provide oxygen or other medications to the intubated patient.

The long arm 51 of the double swivel elbow 4 possesses a junction 9 to allow for complete rotation of the double swivel elbow 4. In certain embodiments, the junction 9 allows for free rotation of the short arm 50 as compared to the long arm 51. In other embodiments, the components are fixed. The long arm 51 of the double swivel elbow 4 further optionally possesses an accordion structure 7 to allow for further rotation and movement of the double swivel elbow 4. For example, the accordion structure 7 can allow for flexible rotation, angled orientation of the components, and provides for a component that allows for a high range of motion and flexibility to safely insert and intubate a patient, while allowing for range of motion. For example, the extension feature 52 along the longitudinal axis of the long arm 51 allows for extension of the double swivel elbow 4 away from the face of the patient. Alternatively, the rotation or angling of the accordion structure 7 can angle according to 53. The angle should be able to extend at least 90 degrees, and preferably up to 180 degrees, where such angle can be generated along any orientation of the accordion structure 7. The ability to angle imparts additional flexibility to the use of the tube, because it allows for secure operation of the rescue breathing tube 1 while reducing the risk of extubation of the patient. At the end of the long arm 51 is the long arm end 6, for mating to a breathing device, such as a mask, endotracheal tube, or other device for positioning in the airway of a patient.

On one portion of the short arm 50 is gas line attachment feature 30. This allows direct connection of a typical oxygen line to the double swivel elbow 4. Typically, this can be used once a patient is to a safe setting and oxygen is available to assist in treating the patient. Other gasses can be administered through this line, as known to those of skill in the art.

Figure 10A:
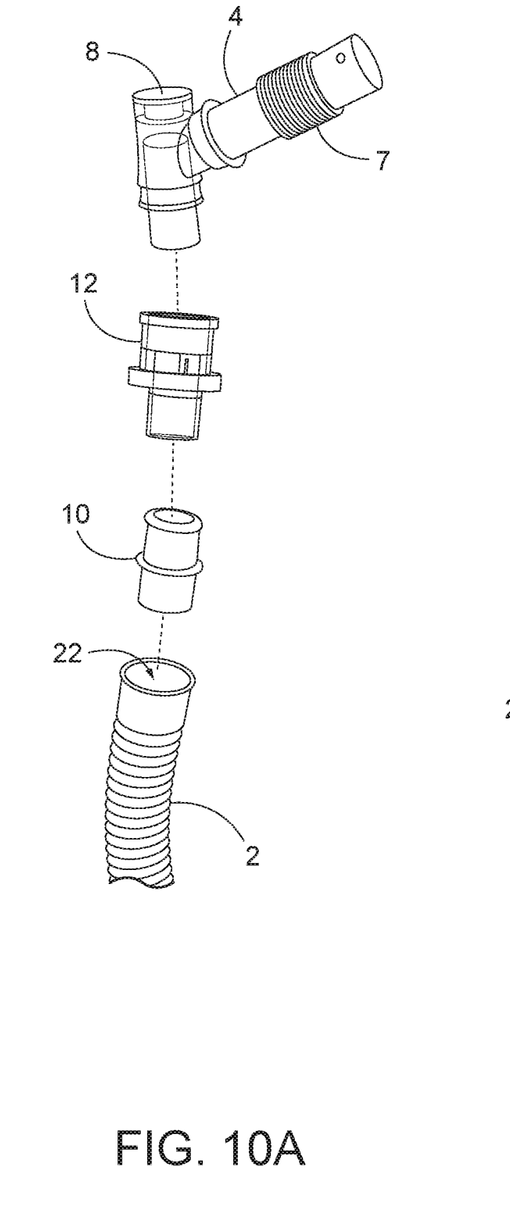
FIGS. 10A and 10B depict various exploded views of opposing ends of a rescue breathing apparatus.
Figure 10B:
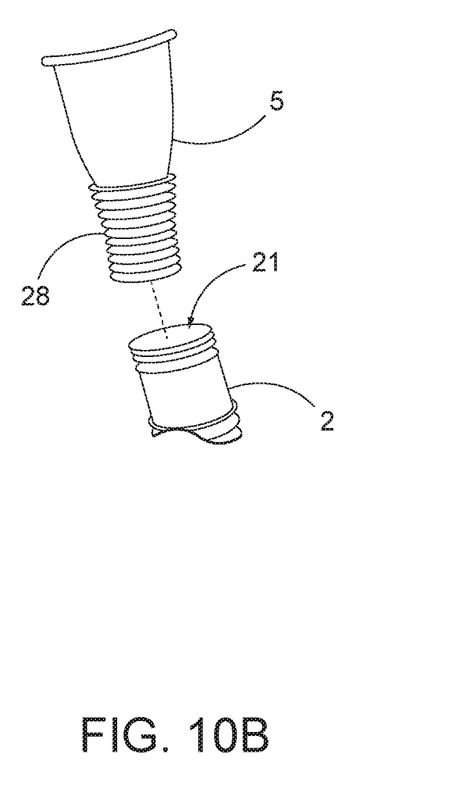

FIGS. 10A and 10B show each of the ends of the tube 2. For example on the proximal end 22 are merely repeated to the adaptor 10, in line with the one-way check valve 12, and then attaching to the short arm end 5 of the double swivel elbow 4. 10B, conversely shows the distal end 21 connecting to the mouthpiece 15.

Figure 11:
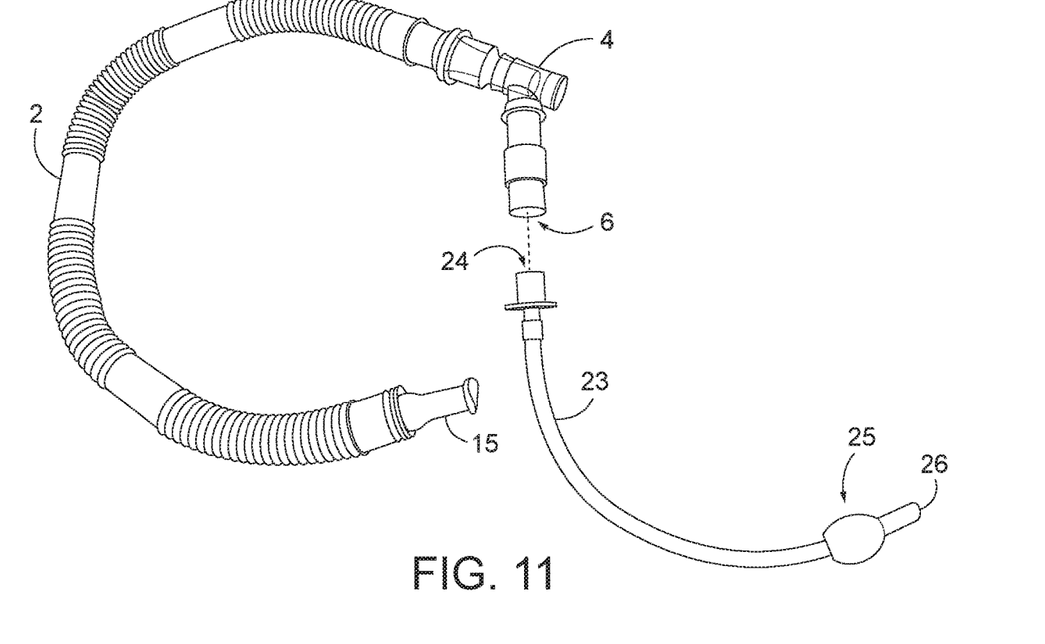
FIG. 11 depicts a rescue breathing apparatus with an endotracheal tube.

FIG. 11 details a complete rescue tube being attached to an endotracheal tube 23. Those of skill in the art will recognize that the endotracheal tube 23 functions by a small diameter tube having a soft distal end 26 and a balloon 25 near the distal end 26, which is inflated by an airline to assist in air flowing through the tube and not around the tube. Furthermore, this balloon 25 assists in maintain the positioning of the endotracheal tube. At the proximal end 24, the tube contains an opening of sufficient diameter to mate with the long arm opening 6.

FIG. 12 details a further embodiment that replaces the mouthpiece 15 with a breathing bag 40. The breathing bag 40 contains an aperture opening 40 to mate with an adaptor 10. The bag 40 contains a hand strap 42 to assist a user with holding the bag 40 and compressing it repeatedly. At the tail end of the bag 40 is an oxygen reservoir 43 that can be filled with oxygen to increase the oxygen given through the manual compressions of the bag. Here, at the distal end 21 the adaptor 10 is necessary to allow for exchange of the mouthpiece 15 to the bag 40.

In certain embodiments, the diameter of the tube 2 is such that no adapter 10 is required. Indeed, the adapter may include several different diameter adapters 10, wherein one end is of constant diameter, able to insert into the tube, while the other end has an outer diameter and an inner diameter, each of which can connect to a secondary device. Several adapters 10 can be included with a kit, each having a different outer and inner diameters of the opposing end, to allow for a variety of secondary devices to be inserted therein. Certain secondary devices will fit directly into the tube 1 and thus the adapters 10 are optional for these features. The adapters 10 may further include locking or latching mechanisms, to selectively attach and detach secondary devices. For example a breathing bag may selectively snap into place and remain securely connected, but may be optionally removed, if the breathing bag 40 is no longer needed, but connection to a different breathing apparatus would be advantageous.

Adapters are particular useful, however, to allow the tube to be a multi-purpose material. Accordingly, the adapters allow for a plurality of components to be interchanged, as necessary, for the particular application of the breathing tube.

As depicted in FIG. 11, the rescue breathing device 1 allows for connection to an endotracheal tube 23, without the requirement that a breathing bag be directly attached. Indeed, the mouthpiece, being attached at the distal end 21 of the tube 2, allows for several inches, to more than a foot, separation from the patient's endotracheal tube 23 to a device that is allowing a rescuer to provide air. The mouthpiece 15 is particularly advantageous as it allows for direct breathing to be given, and does not require additional elements. In tactical situations, or areas where immediate intubation is necessary, such a device can ensure that the patient is receiving oxygen while being safely removed from the situation, to receive additional care. Accordingly, the rescue breathing tube 1 can be utilized a distance away from the patient and leaves both hands for a rescuer free to work with the patient. This enables a wider range of user opportunities, than any existing technology.

Furthermore, this extra space can also be used in certain rescue situations. For example, in the situation where an injured patient is in a space constrained position, due to a building collapse, due to a car accident, a military situation, or the like, the rescue tube can be attached to a breathing tube, and inserted into in small space for rescue breathing, wherein the bag may not easily fit in that space, or cannot be angled properly to allow for attachment. Accordingly, to provide rescue breathing, a rescuer can breathe directly into the opposed end of the flexible tubing 2. Alternatively, the rescuer can breathe directly into a mouthpiece 15, which can be attached to the tube, to allow for hands free breathing to the patient. Similarly, a bag 40 can be attached at the distal end 21 of the rescue tube and allow for compression of the bag to provide the air to the patient. In each case, the rescue tube provides for both stability of the breathing tube, as well as a flexible attachment to the breathing tube to provide mouth or bag generated air to the patient.

A further benefit of the rescue tube, whether use with a mouthpiece or with an attached bag 40, is that because of the flexibility of both the accordion structure 7 and of the flexibility of the tube 2, the tube 2 itself can freely move, while maintaining the endotracheal tube 23 in a stable spot within the patient. This is in direct contrast to the normal occurrence for a bag, which can easily move the endotracheal tube 23. Of course, this is a problem as a patient may be extubated in error, forcing rescuers to stop and re-insert the breathing tube to the patient. Furthermore, the bag may not easily connect to the breathing tube, thus forcing the rescuers to manipulate the patient or have a compromised bag (i.e. mostly compressed, or poorly attached), thus resulting in shallow or weak breaths to the patient.

Therefore, the rescue tube 1 provides for several benefits that are not seen in the prior art. First the tube provides for a flexible and accordion like structure to allow for total flexibility and movement of the tube, even when connected to the breathing tube on the patient. The distal end 21 of the rescue tube can then be open, for direct breaths from a rescuer, or can be attached to a mechanical lung, or attached to a bag, for providing oxygen rich air to the patient, and forcing air into the lungs. This provides for hands free operation of the rescue breathing tube 1. Second, because of the small structure, the rescue breathing tube 1 can fit into small spaces or locations, and can allow for easier attachment to an endotracheal tube 23 and therefore attached to the patient regardless of the position of the patient. Finally, the flexible nature of the device prevents unintentional removal of the breathing tube.

Another way that the rescue tube can be utilized in a hands-free manner is to attach the rescue tube to an airway adjunct, and connect the opposing end to a breathing bag. Because of the flexibility and length of the rescue tube, the bag can be placed under and arm, between the body, and then compressed to provide air to the patient. The bag could also be placed between an arm or body and another accessory.

The rescue tube can therefore be utilized in a method to provide oxygen to a patient comprising, inserting an airway adjunct to said patient, attaching to said airway adjunct a rescue tube, providing air into said rescue tube to provide air to said patient.

The invention as described herein can be modified based on the knowledge of a person of ordinary skill in the art with components that form the same or similar function. Those of skill in the art will recognize such possible variations and that these variations do not take away from the embodiments of the invention as described herein.

A method of providing a rescue breath to a patient comprising: attaching a rescue tube as described herein, to an endotracheal tube inserted into said patient; breathing into a distal end 21 of the rescue tube, wherein said breathing forces air from a mouthpiece 15 through a flexible tube 2, through a one-way valve 12, into a double swivel elbow 4, and finally into the endotracheal tube 23.

Those of skill in the art will recognize that the components are made of medical grade materials, each of which are capable of being sterilized for use. In preferred embodiments, the materials are fitted together, either with and adhesive or friction fit, and sterilized. The sterilized device can be packaged and then sterile components can be utilized as needed. Accordingly, these devices, after use, can then be recycled or destroyed, or alternatively re-sterilized for future use.

Components are also sold as a kit, allowing for the components to be assembled based on the particular needs of a user.

In preferred embodiments, the device provides for rescue breathing use, while allowing for the rescuer to maintain free hands. A method of providing rescue breathing, therefore comprises inserting an air adjunct to the patient; attaching the rescue breathing device, and imparting air through the rescue breathing device to the patient, forcing air to the patient and letting the patient exhale before providing a further and successive breaths to said patient. The air can be provided via a mouthpiece, and rescue breaths provided by breathing into the mouthpiece. Alternatively, a breathing bag, which compresses air and forces it out of one end of the bag, can also provide air. Similarly, a machine or mechanical device can provide air under sufficient pressure.

What is claimed is:

1. A rescue tube comprising a tube having a proximal end and a distal end, and attached to the proximal end is a one-way valve, said one-way valve having a flow end and a check end, and allowing flow of air from the distal end to the proximal end, and attached to the check end of the one-way valve is a ported double swivel elbow having a "y" shape and comprising a long arm and a short arm, and wherein the long arm and the short arms are attached at an angle with a passage allowing passage of gas through a short arm end and a long arm end via an opening at each of the long arm end and the short arm end, wherein the opening at the short arm end is attached to the check end of the one-way valve, and further comprising a self-sealing port at an opposing end of the short arm end; wherein the long arm comprises an accordion structure capable of extending in length and flexing at least 90 degrees, and the opening at the long arm end is suitable for connection to a breathing device; and wherein connected to the distal end of said tube is a mouthpiece.

2. The rescue tube of claim 1 further comprising a first adapter disposed of between the proximal end of said tube and the flow end of the one-way valve.

3. The rescue tube of claim 1 further comprising a second adapter disposed of on the distal end between the distal end of the tube and the mouthpiece.

4. The rescue tube of claim 1, wherein said breathing device is an airway adjunct.

5. The rescue tube of claim 4, wherein said airway adjunct is an endotracheal tube.

6. A method of providing rescue breathing to a patient comprising intubating said patient with an airway adjunct; attaching to said airway adjunct is a rescue tube comprising a tube having a proximal end and a distal end, and attached to the proximal end is a one-way valve, said one-way valve having a flow end and a check end, and allowing flow of air from the distal end to the proximal end, and attached to the check end of the one-way valve is a "y" shaped, ported double swivel elbow having a long arm and a short arm, and wherein the long arm and the short arms are attached at an angle with a passage allowing passage of gas through a short arm end and a long arm end via an opening at each of the short arm end and the long arm end, said short arm further comprising a self-sealing port at an opposing end of the short arm end, and said long arm comprising an accordion structure capable of extending in length and flexing at least 90 degrees, wherein the opening at the short arm end is attached to the check end of the one-way valve, wherein the opening at the long arm end is connected to the airway adjunct; and wherein connected to the distal end of said tube is an air imparting component capable of forcing air through the tube and into the airway adjunct; forcing air through the tube and into the airway adjunct to generate a breath to the patient; allowing the patient to exhale the forced air.

7. The method of claim 6, wherein the air imparting component is a mouthpiece.

8. The method of claim 7, wherein a second person breathes into the mouthpiece to force air through the tube.

9. The method of claim 6, wherein the air imparting component is a breathing bag.

10. The method of claim 9, wherein the breathing bag is compressed to force air through the tube.

11. A rescue tube comprising a length of flexible tubing, defining a passage between a proximal end and a distal end of said tube, and attached to the proximal end of said tube is a one-way valve, said one-way valve having a flow end and a check end, with said one-way valve oriented with the proximal end of said tube engaged to the flow end of said one-way valve thereby allowing flow of air from the distal end to the proximal end of said tube, and attached to the check end of the one-way valve is a "y" shaped ported double swivel elbow having a long arm and a short arm, and wherein the long arm and the short arms are attached at an angle with the passage allowing passage of gas through a short arm end and a long arm end via an opening at each of the short arm end and the long arm end, wherein said long arm comprises an accordion structure capable of extending in length and flexing at least 90 degrees and said short arm further comprises a self-sealing port at an opposing end of the short arm end, wherein the opening at the short arm end is attached to the check end of the one-way valve, wherein the opening at the long arm end is suitable for connection to a breathing device; and wherein connected to the distal end of said tube is air imparting structure.

12. The rescue tube of claim 11, said tube having an inner diameter between 10 and 25 mm.

13. The rescue tube of claim 11, further comprising an adaptor defined to connect between the proximal end of said tube and said one-way valve.

14. The rescue tube of claim 11, further comprising an adaptor defined to connect to the distal end of said tube, and wherein the air imparting structure is connected to said adaptor.

15. The rescue tube of claim 14, wherein said air imparting structure is selected from: a mouthpiece; said mouthpiece comprising an insertion end connected to said adaptor, and a breath giving end; said breath giving end comprising a flange, a breathing bag, or a mechanical air flow generating machine.

* * * * *